United States Patent
Jones et al.

(10) Patent No.: US 9,017,366 B2
(45) Date of Patent: Apr. 28, 2015

(54) METHODS AND SYSTEMS FOR PERFORMING INTRALUMENAL PROCEDURES

(75) Inventors: Donald K. Jones, Dripping Springs, TX (US); Vladimir Mitelberg, Austin, TX (US)

(73) Assignee: Empirilon Technology, LLC, Dripping Springs, TX (US)

( * ) Notice: Subject to any disclaimer, the term of this patent is extended or adjusted under 35 U.S.C. 154(b) by 56 days.

(21) Appl. No.: 13/589,130

(22) Filed: Aug. 18, 2012

(65) Prior Publication Data

US 2013/0046327 A1     Feb. 21, 2013

Related U.S. Application Data

(60) Provisional application No. 61/525,356, filed on Aug. 19, 2011.

(51) Int. Cl.
*A61M 29/00* (2006.01)
*A61B 17/12* (2006.01)
*A61B 19/00* (2006.01)

(52) U.S. Cl.
CPC ..... *A61B 17/12113* (2013.01); *A61B 17/12136* (2013.01); *A61B 17/12145* (2013.01); *A61B 17/1215* (2013.01); *A61B 2017/12054* (2013.01); *A61B 2019/5466* (2013.01)

(58) Field of Classification Search
USPC ......... 623/1.11; 606/191, 108, 192, 194, 195, 606/200, 198; 604/99.01–99.04, 103.07, 604/103.09, 103.1, 103.11, 103.12, 104
See application file for complete search history.

(56) References Cited

U.S. PATENT DOCUMENTS

| | | | | |
|---|---|---|---|---|
| 4,311,146 | A * | 1/1982 | Wonder | 606/195 |
| 5,620,457 | A * | 4/1997 | Pinchasik et al. | 606/194 |
| 6,231,543 | B1 * | 5/2001 | Hegde et al. | 604/96.01 |
| 6,280,457 | B1 * | 8/2001 | Wallace et al. | 606/200 |
| 6,379,329 | B1 * | 4/2002 | Naglreiter et al. | 604/99.02 |
| 2008/0097508 | A1 * | 4/2008 | Jones et al. | 606/191 |
| 2008/0140098 | A1 * | 6/2008 | Kumar et al. | 606/153 |

* cited by examiner

*Primary Examiner* — Jocelin Tanner
(74) *Attorney, Agent, or Firm* — Donald K. Jones

(57) ABSTRACT

Devices, systems and methods are provided for performing implantation procedures in a desired area of the body. Systems include embodiments of medical implants that include scaffold and inflatable portions and delivery systems to position and release the medical implants at a target location within the body.

18 Claims, 5 Drawing Sheets

METHODS AND SYSTEMS FOR PERFORMING INTRALUMENAL PROCEDURES

CROSS-REFERENCE TO RELATED APPLICATION

This application claims the benefit of U.S. Prov. Ser. 61/525,356 filed Aug. 19, 2011 which is hereby incorporated by reference herein in its entirety.

BACKGROUND OF THE INVENTION

The field of intralumenal therapy for the treatment of vascular disease states has for many years focused on the use of many different types of therapeutic devices. While it is currently unforeseeable that one particular device will be suitable to treat all types of vascular disease states it may however be possible to reduce the number of devices used for some disease states while at the same time improve patient outcomes at a reduced cost. To identify potential opportunities to improve the efficiency and efficacy of the devices and procedures it is important for one to understand the state of the art relative to some of the more common disease states.

For instance, one aspect of cerebrovascular disease in which the wall of a blood vessel becomes weakened. Under cerebral flow conditions the weakened vessel wall forms a bulge or aneurysm which can lead to symptomatic neurological deficits or ultimately a hemorrhagic stroke when ruptured. Once diagnosed a small number of these aneurysms are treatable from an endovascular approach using various embolization devices. These embolization devices include detachable balloons, coils, polymerizing liquids, gels, foams, stents and combinations thereof.

Detachable balloons were some of the earliest embolization devices used to treat aneurysms. Under fluoroscopic guidance these balloons were positioned within the aneurysm, inflated using a radio-opaque fluid and subsequently detached from their delivery mechanism. There were numerous drawbacks encountered while using these devices such as difficulty in guiding the devices to the treatment site due to size and shape, difficulties in placing the devices within the aneurysm due to the geometry of the balloons relative to the aneurysm geometry, excessive forces generated during detachment the balloons from the delivery system, dislodging of previously place balloons and delayed deflation of the detached balloons. Examples of various detachable balloon systems attempting to address some of the aforementioned drawbacks are disclosed in U.S. Pat. No. 3,834,394 to Hunter entitled, "Occlusion Device and Method and Apparatus for Inserting the Same", U.S. Pat. No. 4,085,757 to Pevsner entitled, "Miniature Balloon Catheter Method and Apparatus, U.S. Pat. No. 4,327,734 to White Jr. entitled, "Therapeutic Method of Use for Miniature Detachable Balloon" U.S. Pat. No. 4,364,392 to Strother entitled "Detachable Balloon Catheter", U.S. Pat. No. 4,402,319 to Handa, entitled, "Releasable Balloon Catheter", U.S. Pat. No. 4,517,979 to Pecenka, entitled, "Detachable Balloon Catheter", U.S. Pat. No. 4,545,367 to Tucci entitled, "Detachable Balloon Catheter and Method of Use", U.S. Pat. No. 5,041,090 to Scheglov entitled, "Occluding Device" and U.S. Pat. No. 6,379,329 to Naglreiter entitled, "Detachable Balloon Embolization Device and Method." Although the presented detachable balloon systems and improvements are numerous, few have been realized as commercial products for aneurysm treatment largely due to an inability to address a majority of the previously mentioned drawbacks.

The most widely used embolization devices are detachable embolization coils. These coils are generally made from biologically inert platinum alloys. To treat an aneurysm, the coils are navigated to the treatment site under fluoroscopic visualization and carefully positioned within the dome of an aneurysm using sophisticated, expensive delivery systems. Typical procedures require the positioning and deployment of multiple embolization coils which are then packed to a sufficient density as to provide a mechanical impediment to flow impingement on the fragile diseased vessel wall. Some of these bare embolization coil systems have been describe in U.S. Pat. No. 5,108,407 to Geremia, et al., entitled, "Method And Apparatus For Placement Of An Embolic Coil" and U.S. Pat. No. 5,122,136 to Guglielmi, et al., entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils at predetermined positions within vessels of the human body in order to treat aneurysms, or alternatively, to occlude the blood vessel at a particular location. Many of these systems, depending on the particular location and geometry of the aneurysm, have been used to treat aneurysms with various levels of success. One drawback associated with the use of bare embolization coils relates to the inability to adequately pack or fill the aneurysm due to the geometry of the coils which can lead to long term recanalization of the aneurysm with increased risk of rupture.

Some improvements to bare embolization coils have included the incorporation of expandable foams, bioactive materials and hydrogel technology as described in the following U.S. Pat. No. 6,723,108 to Jones, et al., entitled, "Foam Matrix Embolization Device", U.S. Pat. No. 6,423,085 to Murayama, et al., entitled, "Biodegradable Polymer Coils for Intraluminal Implants" and U.S. Pat. No. 6,238,403 to Greene, et al., entitled, "Filamentous Embolic Device with Expansible Elements." While some of these improved embolization coils have been moderately successful in preventing or reducing the rupture and re-rupture rate of some aneurysms, the devices have their own drawbacks. For instance, in the case of bioactive coils, the materials eliciting the biological healing response are somewhat difficult to integrate with the coil structure or have mechanical properties incompatible with those of the coil making the devices difficult to accurately position within the aneurysm. In the case of some expandable foam and hydrogel technology, the expansion of the foam or hydrogel is accomplished due to an interaction of the foam or hydrogel with the surrounding blood environment. This expansion may be immediate or time delayed but is generally, at some point, out of the control of the physician. With a time delayed response the physician may find that coils which were initially placed accurately and detached become dislodged during the expansion process leading to subsequent complications.

For many aneurysms, such as wide necked or fusiform aneurysms the geometry is not suitable for coiling alone. To somewhat expand the use of embolization coils in treating some wide necked aneurysms, stent like scaffolds have been developed to provide support for coils. These types of stent like scaffolds for use in the treatment of aneurysms have been described in U.S. Pat. No. 6,605,111 to Bose et al., entitled, "Endovascular Thin Film Devices and Methods for Treating Strokes" and U.S. Pat. No. 6,673,106 to Mitelberg, et al., entitled, "Intravascular Stent Device". While these stent like devices have broadened the types of aneurysms amenable to embolization therapy, utilization of these devices in conjunction with embolization devices is technically more complex for the physician, may involve more risk to the patient and have a substantial cost increase for the healthcare system.

To further expand the types of aneurysm suitable for interventional radiological treatment, improved stent like devices have been disclosed in U.S. Pat. No. 5,824,053 to Khosravi et al., entitled, "Helical Mesh Endoprosthesis and Method", U.S. Pat. No. 5,951,599 to McCrory, entitled, "Occlusion System for the Endovascular Treatment of and Aneurysm" and U.S. Pat. No. 6,063,111 to Hieshima et al., entitled, "Stent Aneurysm Treatment System and Method." When placed across the neck of an aneurysm the proposed stent like devices purport to have a sufficient density through the wall of the device to reduce flow in the aneurysm allowing the aneurysm to clot, while at the same time having a low enough density through the wall to allow small perforator vessels adjacent to the aneurysm to remain patent. Stent devices of this nature while having the potential to reduce treatment costs have not been realized commercially due to the difficulty in manufacturing, reliability in delivering the devices to the treatment site and an inability to properly position the more dense portion of the stent device accurately over the neck of the aneurysm.

SUMMARY OF THE INVENTION

The present invention is directed toward a medical implant system for use in placing a medical implant at a preselected site within the body of a mammal. In accordance with one aspect of the present invention there is provided an embolization system for use in a mammal. The embolization system includes an elongate flexible delivery system coupled to an embolization device. The elongate filamentous or filament like embolization device comprises an elongate embolic coil member coupled to an expandable embolic balloon member. The embolization device generally resembles a long flexible strand having a generally elongated linear configuration when delivered through the lumen of a catheter and is capable of folding upon itself during placement at a target site in the body. The delivery system includes an elongate tubular filling member positioned within the lumen of an elongate tubular positioning member both having proximal and distal ends and wherein the distal end of the filling member is removably coupled to the embolic balloon member and adapted to provide fluid access to the interior of the balloon member. A valve member (normally biased closed) is included with the balloon member such that when sufficient fluid has been delivered to expand the balloon member to a desired volume, the tubular filling member may be uncoupled from the balloon member thereby allowing the valve member to seal the balloon member and maintain the balloon member inflation.

In accordance with another aspect of the present invention there is provided an elongate filamentous embolization device having an elongate filamentous scaffold portion and an expandable portion where the expandable portion includes an elongate balloon member and the scaffold portion takes the form of a radiopaque embolic coil.

In accordance with yet another aspect of the present invention there is provided a medical implant having a coating that includes bioactive materials. The bioactive materials may include bioerodible and or biodegradable synthetic materials. The coating may be preferably applied to the exterior of the device and further comprise one or more pharmaceutical substances or drug compositions for delivering to the tissues adjacent to the site of implantation, and one or more ligands, such as peptides which bind to cell surface receptors, small and/or large molecules, and/or antibodies or combinations thereof for capturing and immobilizing, in particular progenitor endothelial cells on the blood contacting surface of the device to promote healing.

In accordance with yet another aspect of the present invention there is provided an embolization device having an elongate filamentous scaffold portion and an expandable portion where the expandable portion includes a balloon member having a length that extends substantially the length of the embolic coil. The length of the scaffold portion or embolic coil is preferably greater than ten times the diameter of the inflated expandable portion or balloon member. Additionally, the balloon member may include regions along its length that limit or restrict expansion.

In accordance with still another aspect of the present invention, there is provided a method of deploying a medical implant within a portion of a vessel. The method comprises the steps of: positioning a catheter adjacent a target site; delivering an embolization system having an embolization device and delivery system to the target site; deploying the embolization device at the target site; inflating the embolization device with a fluid to increase the volume of a portion of the embolization device; releasing the embolization device from the delivery system; sealing the inflated portion of the embolization device; removing the delivery system and catheter from the patient.

DETAILED DESCRIPTION OF THE INVENTION

Figure 1:
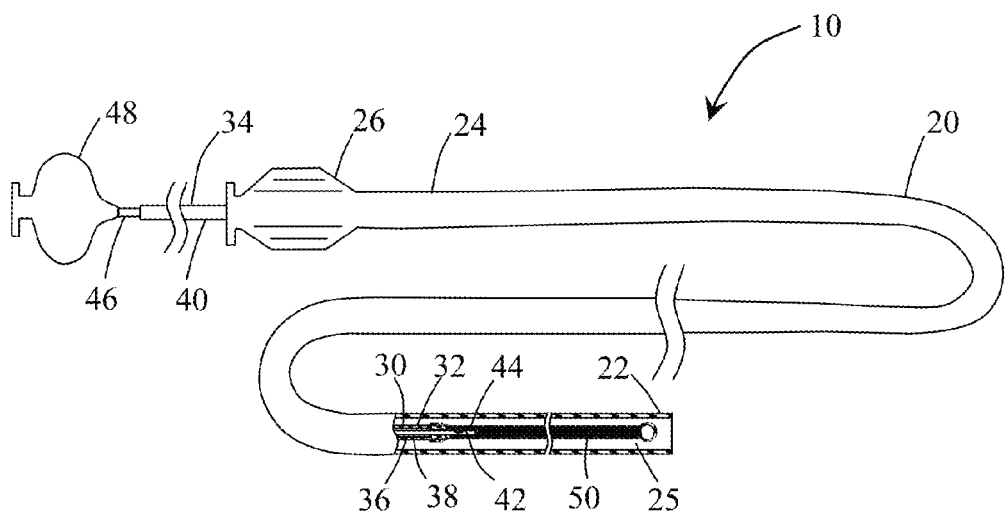
FIG. 1 is a partially sectioned view of an embodiment of a medical implant system of the present invention.
Figure 2:
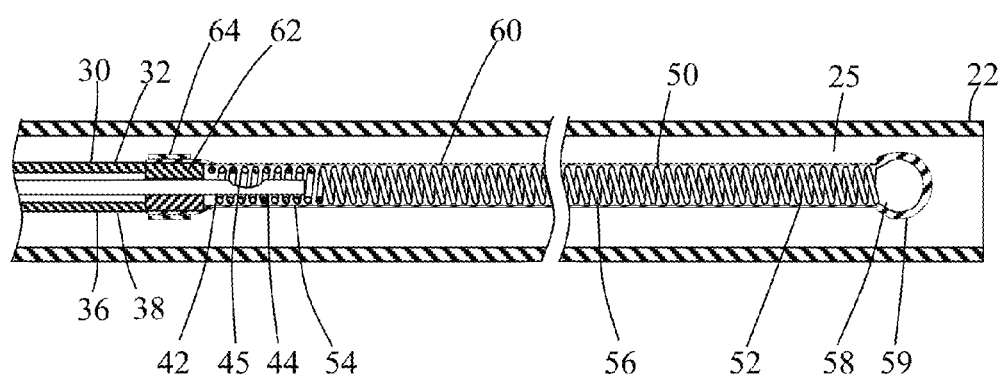
FIG. 2 is an enlarged partially sectioned view illustrating the distal portion of the medical implant system shown in FIG. 1.

Generally a medical implant deployment system of the present invention may be used to position an implant at a preselected site within the body of a mammal. FIG. 1 generally illustrates embolization system 10 of the present invention which includes elongate catheter 20 having distal and proximal ends 22, 24 and lumen 25 extending therethrough. Proximal end 24 includes catheter hub 26 to facilitate access to lumen 25. Additionally hub 26 includes a Luer connector to facilitate connections with accessory devices commonly used in interventional radiological procedures such as, rotating hemostatic valves. While not shown, the construction of catheter 20 may utilize known catheter technologies that incorporate braiding and or coiling using metallic or non-metallic reinforcing filamentous materials to provide high strength while maintaining catheter flexibility. The term "filamentous" as used herein may be used to describe an object a) composed of or containing filaments b) pertaining to or resembling a filament or c) bearing filaments. The aforementioned definition b) pertaining to or resembling a filament is understood to include general observations of filaments having a substantially longer length relative to its diameter. The incorporation of lubricious hydrophilic and or hydrophobic materials on the inner and or outer surface of the catheter and the application of tip markers are considered to be within the scope of known catheter construction techniques and suitable for uses herein described. Delivery system 30 having distal and proximal ends 32, 34 includes an outer tubular positioning member 36 having distal and proximal ends 38, 40 and an inner tubular filling member 42 having distal end 44, aperture 45 and proximal end 46. Filling member 42 includes hub 48 coupled to proximal end 46 to facilitate coupling to syringes or other fluid delivery sources. Delivery system 30 is positioned within lumen 25 of catheter 20 such that proximal end 34 extends proximal to catheter hub 26. FIG. 2 depicts embolization device 50, having distal and proximal portions 52, 54, which is coupled to delivery system distal end 32 in a removable fashion. Embolization device distal portion 52 includes a scaffold member that takes the form of elongate embolic coil 56 having a traumatic distal end 58. Distal portion 52 of embolization device 50 includes joint member 59 which couples the distal end of embolic coil 56 to expandable balloon member 60. Expandable balloon member 60 includes a proximal sealing valve 62 and a tubular retaining element 64 positioned around valve 62. Distal end 44 of filing member 42 is positioned through sealing valve 62 such that aperture 45 is in fluid communication with balloon member 60. Sealing valve 62 is formed of a resilient material and has a normally closed configuration such that when filling member distal end 44 is withdrawn from sealing valve 12 the sealing valve closes. The resiliency of sealing valve 62 provides a frictional engagement between the valve and distal end 44 of filling member 42. Retaining element 64 preferably takes the form of a radiopaque shrink tubing or marker band to provide visibility under fluoroscopy of the proximal end of embolization device 50 and to restrict the expansion of sealing valve 62 thus providing increased frictional engagement between the sealing valve and filling member distal end 44. Distal end 38 of pusher member 36 is positioned adjacent sealing valve 62 and retaining element 64. Positioning member 36 is preferably formed of a thin walled metallic hypotube however catheter construction materials and techniques may also be suitable. Preferably, distal end 38 of pusher member 36 is flexible but resists axial elongation and compression and has an outer diameter close to the diameter of sealing valve 62. Filling member 42 is also preferably formed of a thin walled metallic hypotube however catheter construction materials and techniques may also be suitable.

Embolic coil 56 is shown in FIG. 2 adjacent to expandable balloon member 60 and more specifically in a preferred arrangement of embolization device 50, at least a substantial portion of the length of coil 56 is positioned within the interior of balloon member 60. In an alternative arrangement (not shown), a balloon member may have a length substantially comparable to the length of an embolic coil scaffold member, fixedly coupled to the coil however, the scaffold member is not substantially positioned within the interior of the balloon member. In this alternative arrangement, the balloon member and the scaffold member are side by side extending generally parallel to each other during delivery through a catheter lumen.

Figure 3A:
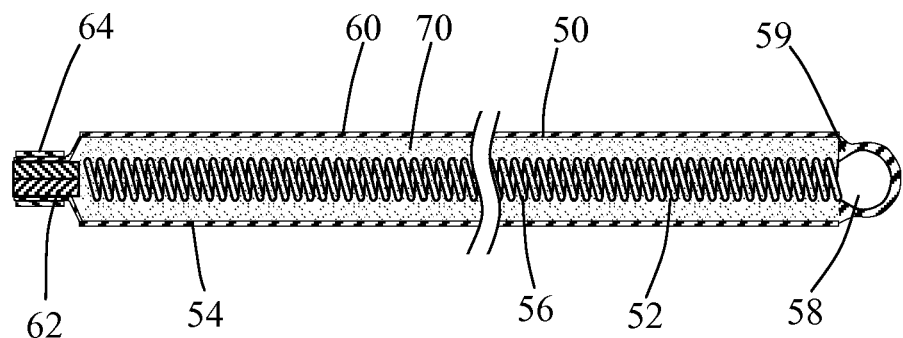
FIG. 3A is a partial cross-sectional view of an embolization device according to an embodiment of the present invention.

FIG. 3A illustrates embolization device 50 where balloon member 60 has been expanded and sealing valve 62 is closed. Embolic coil 56 of embolization device 50 is typically formed from a helically coiled wire using suitable biocompatible materials such as platinum, nitinol, gold or stainless steel with platinum being a preferred material. The wire depicted in embolic coil 56 has a preferred cross-sectional geometry which is circular although other shapes such as "D", rectangular and star are also contemplated. Scaffold members such as embolic coil 56 may take other suitable forms such as elongate braids or multi-filar winds. Embolic coil 56 is shown having a generally straight shape for convenience but preferably has a shape and size suited for a target location. Embolic coil 56 has a "primary" coil diameter that ranges from about 0.005 inches to about 0.050 inches and preferably ranges from about 0.008 inches to about 0.040 inches. The length of embolic coil 56 may vary widely and ranges from about 1 cm to about 150 cm with a preferred range of 2 cm to 80 cm. These coils may be formed into helices, spheres or other complex or convoluted shapes having a "secondary" coil diameter ranging from about 2 mm to 50 mm. The selection of the dimensions for a particular coil is dependent upon the dimensions and geometry of the target anatomical site. For example, to treat an aneurysm having a 7 mm diameter, the embolic coil 56 may preferably have a primary coil diameter in the range of 0.010 inches to 0.020 inches and a shape that is helical or generally spherical with a secondary diameter of about 7 mm to 8 mm dependent upon the stiffness of the coil. Embolization device 50 may also include modifications such as the addition of stretch resistance members to aid in delivery, surface texturing and or the addition of bioactive materials and therapeutic compounds as components or coatings to promote the healing response. Other shapes such as spirals and "hour glasses" may be suitable for other lumenal locations within the body.

Figure 3B:
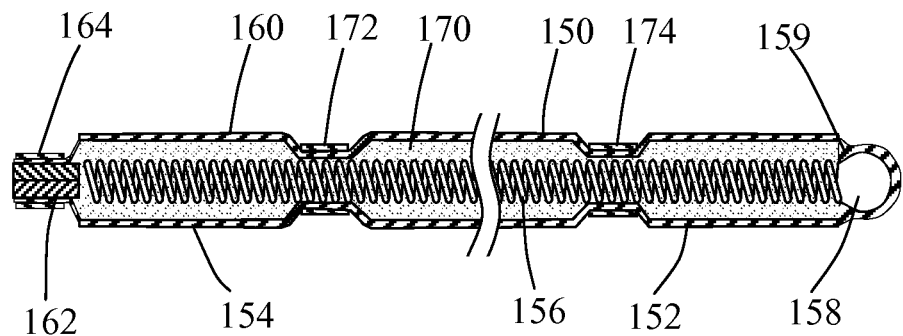
FIG. 3B is a partial cross-sectional view of an embolization device according to another embodiment of the present invention.

An alternative embodiment of an embolization device is shown in FIG. 3B where embolization device 150 having balloon member 160 includes expansion resisting elements 172 and 174. The expansion resisting elements restrict or limit portions of balloon member 160 from expanding during inflation. Expansion resisting elements 172 and 174 are preferably formed as tubular segments of shrink tubing that are positioned around portions of balloon member 160. Alternatively, portions of balloon member 160 may be integrally secured to coil 156 to restrict expansion at that particular location.

Figure 3C:
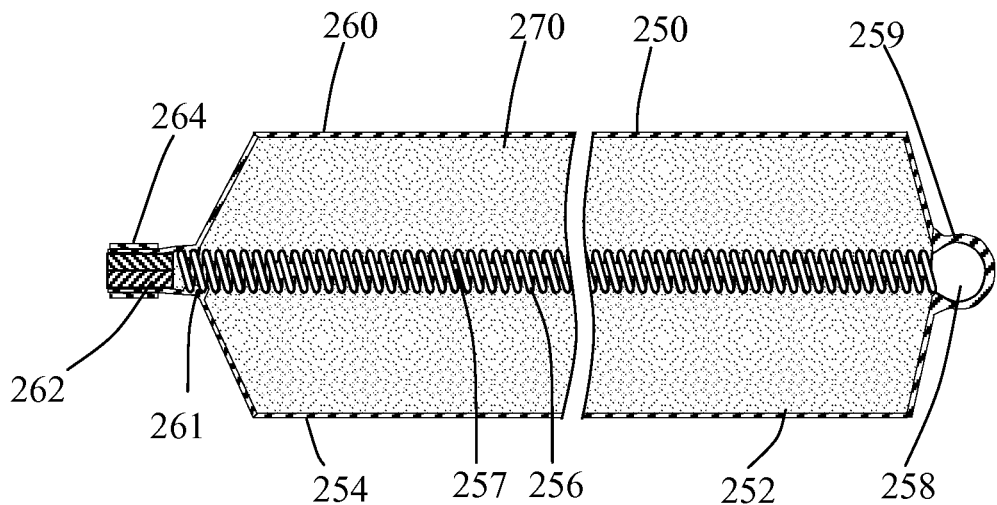
FIG. 3C is a partial cross-sectional view of an embolization device according to yet another embodiment of the present invention.

Another alternative embodiment of an embolization device is shown in FIG. 3C where embolization device 250 having embolic coil 256 includes an elongate shaping wire 257 positioned within the lumen of coil 256. The elongate shaping wire 257 is preferably formed of a resilient material such as nitinol and aids the coil in taking a shape. The shaping wire 257 may be free floating within the lumen of coil 256 or secured at various locations to provide increased stretch resistance.

Balloon member 60, shown in an expanded configuration, may be formed of an elastomeric material such as silicone in a first preferred embodiment having a compliant balloon member and a non-elastomeric material such as polyethylene terephthalate (PET) in a second preferred embodiment having a non-compliant or semi-compliant balloon member. Suitable compliant balloon materials include other polymeric elastomers such as urethanes, polyether block amide (PEBAX) and synthetic rubbers including polyisoprene, nitrile, chloroprene, ethylene propylene diene rubber. Suitable non-compliant or semi-compliant balloon materials include polymers such as nylons, polyolefins and polytetrafluoroethylene (PTFE). Balloon member 60 may be formed by conventional techniques including extrusion and or molding of aforementioned polymers. For non-compliant or semi-compliant balloon members the wall thickness of the balloon member typically ranges from about 0.0001 inches to about 0.003 inches. For compliant balloon members the wall thickness of the balloon member typically ranges from about 0.0005 inches to about 0.006 inches. Embolic coil 56 is positioned within balloon member 60 and balloon member 60 has a length that extends along a substantial portion of the length embolic coil 56 and may include the entire length of embolic coil 56 as shown in FIG. 3A. Additionally, balloon member 60 may be coated with lubricious hydrophilic and or hydrophobic materials to aid in delivery through lumen of the catheter. Balloon member 60 is preferably inflated with a low viscosity fluid 70 such as saline. Radiopaque fluids such as iodinated contrast solutions may also be suitable and provide the advantage of visibility during inflation. Balloon member 60 may also be inflated using radio-opacified fluids that transition from a liquid to a solid polymerizable or cross linkable solutions such as alginates, cyanoacrylates and monomers of hydroxyl-ethyl methacrylate (HEMA).

One important aspect of embolization devices according embodiments of the present invention that include an elongate filamentous scaffold member and an expandable balloon member is to provide stable volume filling of an anatomical target site greater than the volume filling that can be achieved by the filamentous scaffold alone. It is also advantageous in performing medical procedures that the delivery catheters utilized to deliver embolization devices according to embodiments of the present invention be comparable in size to the delivery catheters used when delivering conventional detachable embolic coil systems. As previously discussed, scaffold members such as embolic coils have a primary diameter, and a relationship between the inflated balloon member diameter and the primary diameter of the scaffold member has been determined to allow for the use of delivery catheters comparable in size to the delivery catheters used with conventional detachable coil systems. In a preferred embodiment having a non-compliant or semi-compliant balloon member the inflated balloon member maximum diameter is greater than 1.2 times the primary diameter of the scaffold and is preferably in the range of 1.5 to 4 times the primary scaffold diameter with a most preferred range of 1.7 to 3.5 times the primary scaffold diameter.

Figure 4:
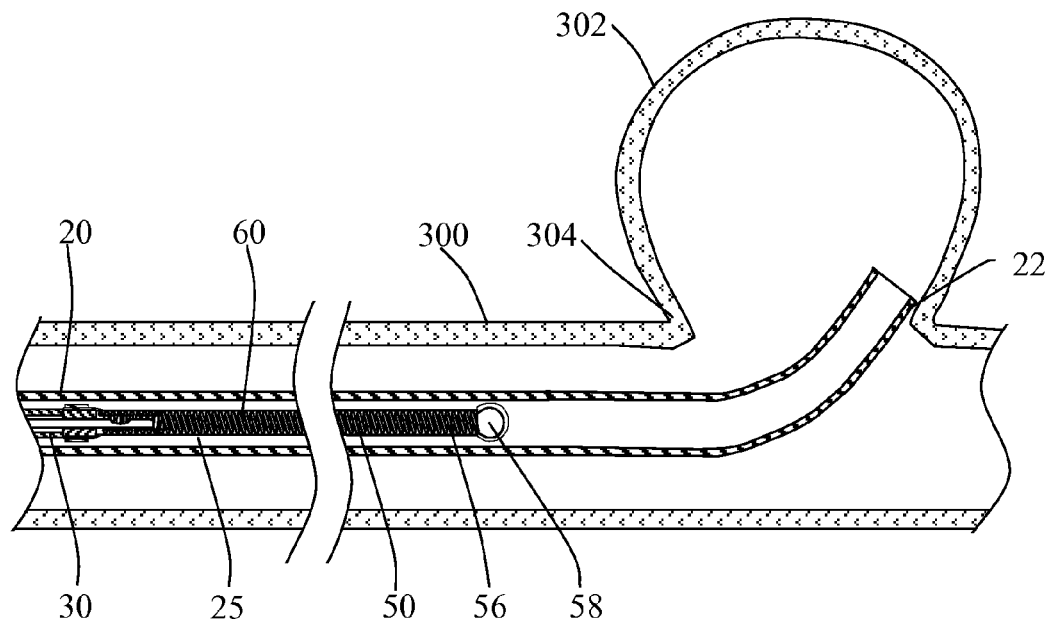
FIGS. 4 through 8 are partial section views illustrating a method of deploying a medical implant within an aneurysm according to an embodiment of the present invention.
Figure 5:
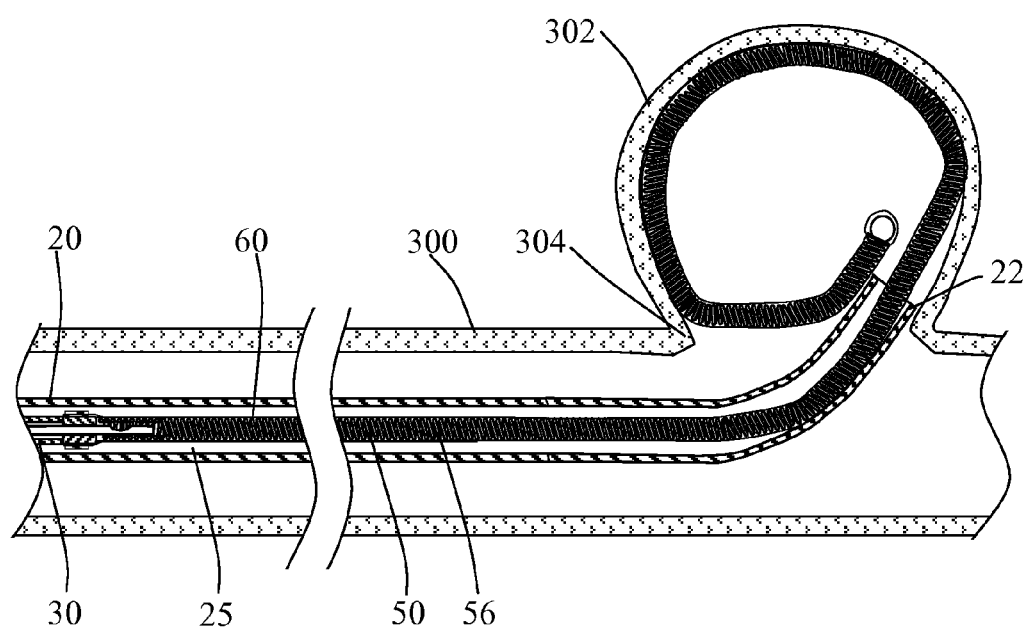
Figure 6:
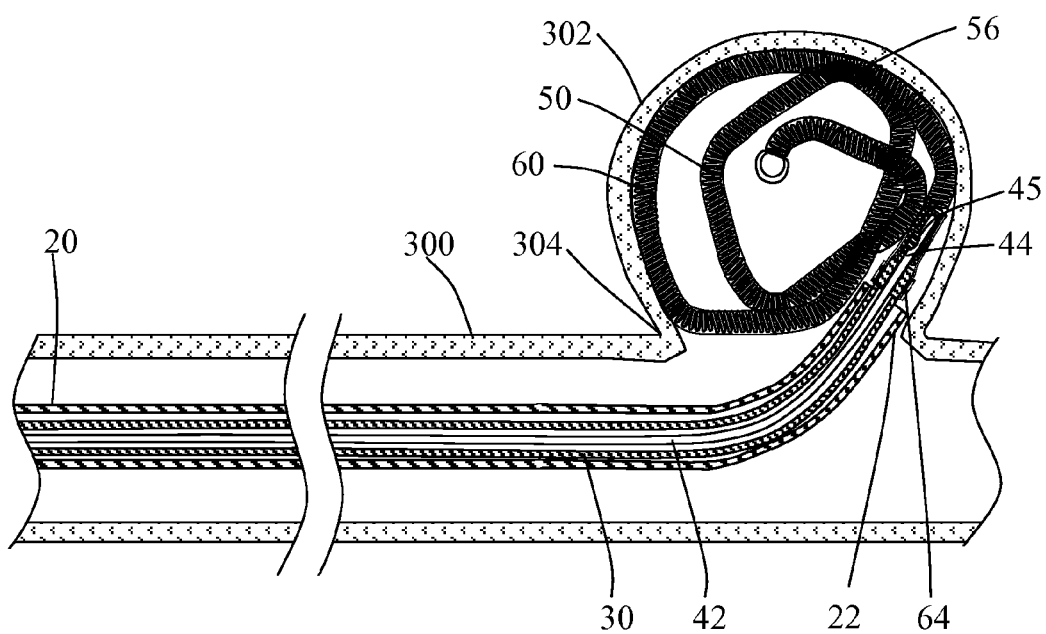
Figure 7:
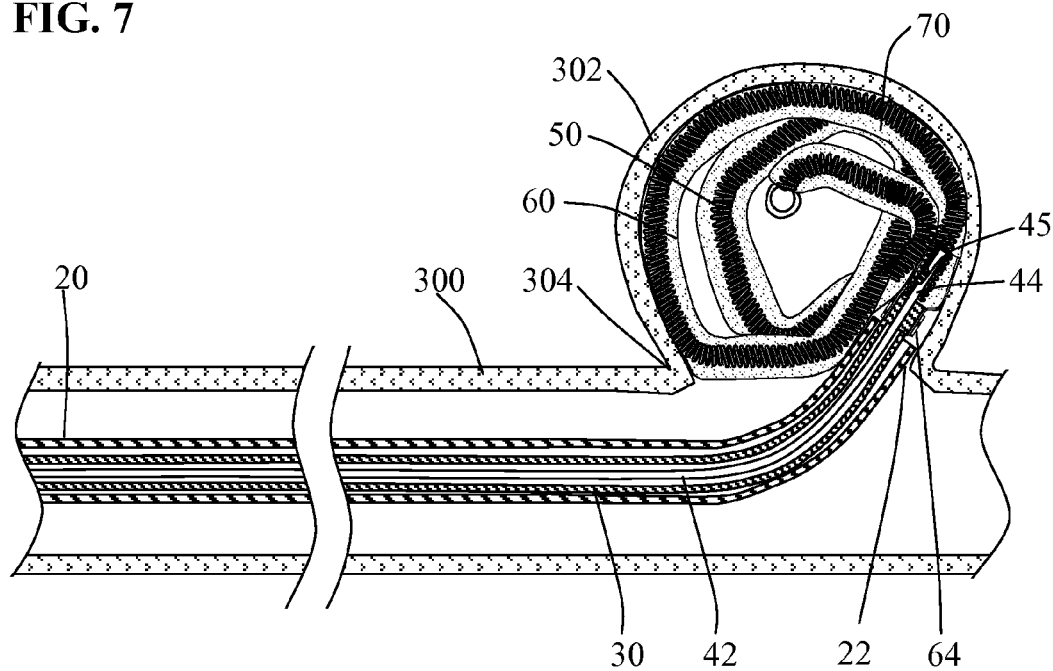
Figure 8:
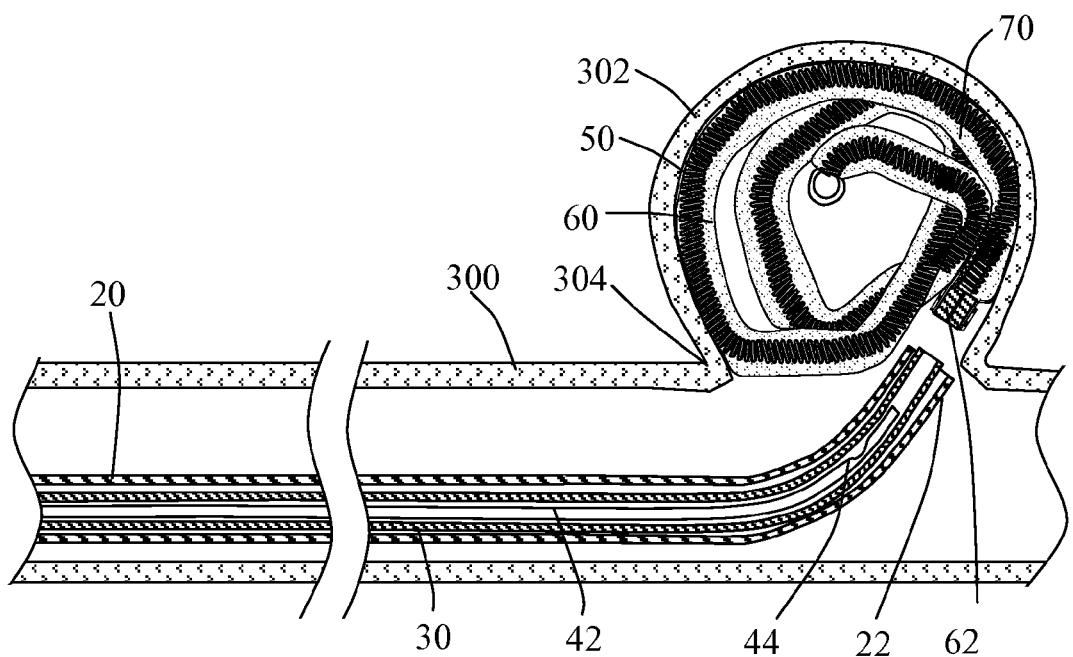

FIGS. 4 through 8 illustrate the method steps of using embolization system 10 to treat an aneurysm of a blood vessel. Embolization system 10 is inserted into blood vessel 300 and catheter 20 is moved to a position within vessel 300 where catheter distal end 22 is positioned within aneurysm 302 adjacent to aneurysm neck 304 (FIG. 4). Embolization device 50 is inserted into the lumen of catheter 20 and has a generally linear configuration. Delivery system 30, coupled to embolization device 50, is advanced distally within catheter 20 such that embolic coil 56 begins to exit catheter lumen 25 and enter aneurysm 302. Further advancement of delivery system 30 allows embolization device 50, which is capable of folding upon itself, to take a shape within aneurysm 302 with embolic coil 56 forming a scaffold or framework supporting balloon member 60. During delivery, the physician may retract and advance delivery system 30 to reposition embolic coil 56 into the desired scaffold geometry. Once embolization device 50 is properly positioned within aneurysm 302 (FIG. 6), a fluid delivery source, such as a fluid filled syringe, is then coupled to filling member hub 48 (not shown). Fluid 70 is delivered to balloon member 60 via filling member 42 to inflate or expand balloon member 60 to a desired volume. It is preferable that fluid 70 is a radiopaque polymerizable liquid, so that the volume filling of balloon member 60 is readily identifiable under fluoroscopy (FIG. 7). Upon achieving the desired filling of balloon member 60, filling member 42 is retracted relative to pusher member 36, withdrawing filling member distal end 44 from balloon member 60 thus uncoupling delivery system 30 from embolization device 50 which allows sealing valve 62 to close and seal. The closed sealing valve 62, maintains the inflation of balloon member 60 and the scaffold created by embolic coil 56 retains balloon member 60 within aneurysm 302. Delivery system 30 may then be removed from catheter 20 and the body. If the volume filling of the aneurysm is determined to be insufficient, the physician may deploy another embolization device into the aneurysm and fill to achieve the desired result, otherwise catheter 20 can be removed.

As is apparent, there are numerous modifications of the preferred embodiment described above which will become readily apparent to one skilled in the art. It should be understood that various modifications including the substitution of elements or components which perform substantially the same function in the same way to achieve substantially the same result may be made by those skilled in the art without departing from the scope of the claims which follow.

That which is claimed is:

1. A medical implant system comprising:
an elongate flexible catheter having proximal and distal ends and a lumen extending therethrough;
a filamentous composite medical implant having proximal and distal ends and an elongate filamentous scaffold portion fixedly coupled to an elongate filamentous balloon portion, said balloon portion including an elongate filamentous balloon member and a valve assembly, said scaffold portion defining a path being positioned within said balloon member and said balloon member having a length that extends over a substantial portion of the length of said scaffold portion, said balloon member having a first configuration and a first diameter when uninflated and a second configuration and a second diameter when inflated with a fluid, said balloon member being selectively operable between said first and second configurations and said second diameter being selectively adjustable wherein said balloon member first and second configurations generally follow path of said scaffold portion; and
an elongate delivery system positioned within the lumen of said catheter including a tubular pusher member having proximal and distal ends and a lumen extending therethrough and a tubular filling member having proximal and distal ends and being slidably positioned within the lumen of said pusher member, said filling member distal end being removably coupled to said medical implant in a first configuration and uncoupled from said medical implant in a second configuration, said filling member being operable between said first configuration and said second configuration whereby proximal movement of said filling member relative to said pusher member in said first configuration causes the distal end of said filling member to retract and uncouple from said balloon portion.

2. A medical implant system according to claim 1 wherein said elongate scaffold includes an embolic coil.

3. A medical implant system according to claim 2 wherein said embolic coil includes a shaping member.

4. A medical implant system according to claim 2 wherein said embolic coil includes a stretch resistant member.

5. A medical implant system according to claim 1 wherein said fluid includes a radiopaque fluid.

6. A medical implant system according to claim 1 wherein said fluid comprises a fluid that transitions from a liquid to a solid.

7. A medical implant system according to claim 1 wherein said balloon member has a maximum inflated second diameter which is between 1.2 and 4 times a diameter of said scaffold portion.

8. A medical implant system according to claim 1 wherein said medical implant includes at least one expansion resisting member positioned at a location along the length of said balloon member to restrict the expansion of said balloon member at said location.

9. A medical implant system according to claim 1 wherein said medical implant is an embolization device and said embolization device has a generally linear first configuration during delivery through said catheter and a shaped second configuration upon deployment at a target site.

10. An embolization device according to claim 9 wherein said embolization device is capable of folding upon itself during deployment.

11. An embolization device according to claim 10 wherein said elongate scaffold member comprises an embolic coil.

12. An embolization device according to claim 11 wherein said balloon member is formed from a semi-compliant material.

13. An embolization device according to claim 11 wherein said embolic coil includes a stretch resistant member.

14. An embolization device according to claim 11 wherein at least one of said balloon member and scaffold member comprises a bioactive therapeutic material.

15. An embolization device according to claim 10 wherein said fluid includes a radiopaque fluid.

16. An embolization device according to claim 10 wherein said fluid comprises a fluid that transitions from a liquid to a solid.

17. An embolization device according to claim 10 wherein said balloon member includes at least one expansion resisting member to restrict the expansion of said balloon member.

18. An embolization device according to claim 10 wherein said shaped second configuration includes complex shapes.

* * * * *